United States Patent
Warwick et al.

[11] Patent Number: 6,050,953
[45] Date of Patent: Apr. 18, 2000

[54] DEVICE AND METHOD FOR MEASURING A SPIROGRAM

[76] Inventors: Warren J. Warwick, 1952 E. River Ter., Minneapolis, Minn. 55414; Leland G. Hansen, 2309 Beverly Rd., St. Paul, Minn. 55104

[21] Appl. No.: 09/082,498

[22] Filed: May 21, 1998

Related U.S. Application Data

[60] Provisional application No. 60/080,562, Apr. 3, 1998.

[51] Int. Cl.[7] ........................................................ A61B 5/08
[52] U.S. Cl. ........................ 600/538; 600/532; 600/531; 73/23.3; 73/31.04
[58] Field of Search ........................ 600/538, 532, 600/531, 529; 73/23.3, 31.04, 28.03

[56] References Cited

U.S. PATENT DOCUMENTS

| | | | |
|---|---|---|---|
| 3,889,672 | 6/1975 | Woldring | 600/538 |
| 3,924,612 | 12/1975 | Dempster et al. | 600/538 |
| 4,034,743 | 7/1977 | Greenwood et al. | |
| 4,178,919 | 12/1979 | Hall | 600/598 |
| 4,736,750 | 4/1988 | Valdespino et al. | |
| 5,058,601 | 10/1991 | Riker . | |
| 5,170,798 | 12/1992 | Riker . | |
| 5,398,695 | 3/1995 | Anderson et al. | 600/538 |
| 5,857,459 | 1/1999 | Snow et al. | 600/538 |
| 5,868,681 | 2/1999 | Schiller . | |

OTHER PUBLICATIONS

Brochure entitled "Portable Spirometry . . . for you–the 2120", Vitalograph, Inc., published on date even with or prior to Apr. 3, 1998, 2 pages.

Brochure entitled "Now You Can Enjoy the Benefits of Spirometry Testing and Dispose of the Pitfalls", QRS, published on date even with or prior to Apr. 3, 1998, 2 pages.

*Primary Examiner*—Max Hindenburg
*Assistant Examiner*—Navin Natnithithadha
*Attorney, Agent, or Firm*—Crompton, Seager & Tufte, LLC

[57] ABSTRACT

A device and method for measuring critical portions of an individual's forced expiratory efforts. The device includes a series of preset negative pressure sensors attached to a sensor port located in a breathing tube of predetermined dimension. A patient blows through the breathing tube triggering the various sensors depending on the airflow rate. The time each of the sensors are activated is recorded. The recorded information can be used to determine various diagnostic parameters.

7 Claims, 4 Drawing Sheets

DEVICE AND METHOD FOR MEASURING A SPIROGRAM

This appln claims the benefit of U.S. Provisional No. 60/080,562, filed Apr. 3, 1998.

BACKGROUND OF THE INVENTION

The present invention relates generally to the field of spirometry. In particular, the invention pertains to a device and method for measuring critical portions of an individual spirogram.

Treatment and diagnosis of individuals with chronic lung disease requires measurement of pulmonary function. Treatment of these individuals requires measurement of the pulmonary function on a routine basis throughout the patients' life. These measurements are useful in the day to day management of diseases such as asthma and Cystic Fibrosis. Pulmonary function measurements may also be useful in the conditioning of athletes where training regiments can be optimized to achieve maximum lung condition. A simple device and method has not been available to measure pulmonary functions, other than a peak flow meter. Traditional spirometry has been used to measure various pulmonary function parameters such as forced expiratory volume in one second (FEV1), peak expiratory flow (PF), forced vital capacity (FVC) and forced expiratory flows at 50% and 75% (FEF25:75). Traditional spirometry forces a patient to exert maximal expiratory effort, i.e., exhale as hard, fast and long as possible. Some patients during traditional spirometry procedures may exhale for as long as 20 seconds or more. Such strenuous effort can be painful and fatiguing, particularly for those suffering from pulmonary disease or dysfunction.

Traditional spirometry has several limitations. These include, for example: (1) the start of the "blow" must be established by back extrapolation; (2) the most reliable measurement, the Forced Expiratory Volume in One Second, has an extrapolated beginning and a convenient, but arbitrary, duration; (3) the Peak Expiratory Flow (PF) is an instantaneous measurement and attainment of maximum value compromises the values for the Forced Vital Capacity (FVC); (4) the FVC has a calculated beginning (#1) and end as well as an arbitrary requirement for its duration; (5) efforts to maximize the FVC cause a decrease in the PF; (6) arbitrary criteria are needed to establish the best efforts; (7) the boundary of the forced expiratory flow volume loop is effort independent, i.e., no effort can increase the size of the curve, but all the "normal" and calculated values are dependent on the observed measurement of the FVC; (8) forced expiratory flows are 50% and at 75% expired are arbitrary and instantaneous points whose "normal" and calculated values are dependent on the magnitude of the FVC; (9) the reliability of spirometric test results is comprised in the very young, old, mentally and physically limited subjects; (10) much effort must be expended to calibrate the spirometer to ensure accurate measurements; (11) reference standards and calculations are based on assumptions of water vapor contents of the expired air which many authors have shown to be imprecise; and (12) current instrumentation is expensive.

SUMMARY OF THE INVENTION

The present invention pertains to a device and method for measuring critical portions of an individuals forced expiratory effort. The device can be used to measure critical portions of a patients forced expiratory effort in a much shorter period and more accurately than traditional spirometry. For example, critical diagnostic criteria may be measured during a three second exhalation or "blow" into the device. The patient will generally blow as hard and fast as possible as in traditional spirometry, but rather than having to blow for an exhaustive period of up to 20 seconds or more, the critical measurements can be obtained in a small percentage of that time, typically less than two seconds. The parameters measured are also believed to be approximately 100% more accurate in the diagnosis of lung disease in patients with Cystic Fibrosis and other lung diseases than traditional spirometry.

The method of the present invention utilizes parameters, such as duration of forced expiration greater than each of the arbitrary air flow rates, in the central range, instead of measuring the extremes, of lung function. This can be done by measuring the duration of time air flow exceeds selected flow rates. The test is sensitive to the presence of both obstructive and restrictive pulmonary problems. The test can be executed by a device that stores date, time and multiple test results, for example, 500 or more results. The results can be downloaded into a computer in a physicians office or other location either directly or remotely by telephone.

In one embodiment of the device in accordance with the present invention, the device includes a series of preset negative pressure sensors attached to a sensor tube located in a breathing tube of predetermined dimension. Blowing through the breathing tube triggers the various sensors "on" and "off" as the flow rate through the tube rises above and drops below the preset negative pressure for each sensor. The time each of the sensors is activated is recorded, providing data which can be used for diagnostic purposes. Numerous calculations can be done to give an accurate picture of several portions of a patient's spirogram.

DETAILED DESCRIPTION OF THE INVENTION

Figure 1:
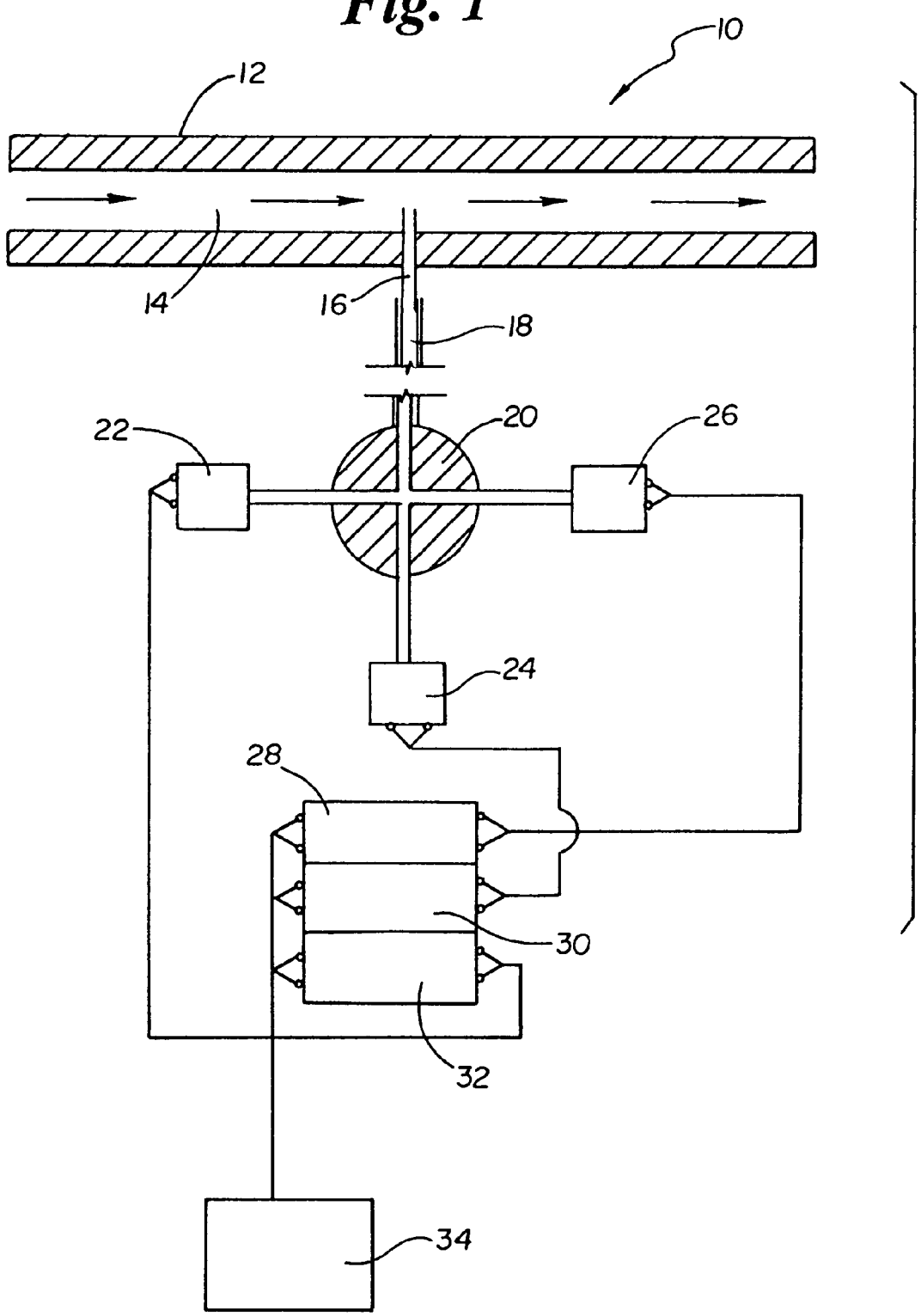
FIG. 1 is a schematic drawing of the device in accordance with the present invention.

Referring now to the drawings wherein like reference numerals refer to like elements throughout the several views, FIG. 1 is a schematic representation of a device 10 in accordance with the present invention. Flow Time Monitor (FTM) device 10 includes a breathing tube 12 defining an elongate lumen 14 therethrough. Tube 12 could be, for example, a delrin tube approximately 7 cm in length with an inside diameter of preferably within the range of about 2 to 20 mm, or more preferably, about 5 to 15 mm, or most preferably, approximately 9.5 mm. Disposed proximate the center of tube 12 is a sensor tube 16. Sensor 16 penetrates the wall of tube 12 at angle approximately perpendicular to the air stream shown by the arrows. Tube 16 may be formed from, for example, a stainless steel hypotube having a 1.3 mm inside diameter and a 1.9 mm outside diameter. The tube preferably extends into lumen 14 approximately 4.5 mm. A flexible polymer tube 18 connects sensor tube 16 to a manifold 20.

Manifold 20 in turn connects, in fluid communication, tube 18 with a plurality of sensors 22, 24 and 26. Sensors 22, 24 and 26 are preferably negative, low pressure sensors or transducers. Such low pressure sensors are available from World Magnetics. The sensors 22, 24 and 26 can be calibrated such that for example, 0.125, 0.249 and 0.373 kPa sensors. are turned on when the flow through lumen 14 equals or exceeds 0.62, 1.32 and 2.21 liters per second respectively and off when the flow rate falls below the respective levels.

Each sensor 22, 24 and 26 is connected to a separate elapsed time meter 32, 30 and 28, respectively. The elapsed time meters can be real devices or virtual devices in a computer program on a computer chip or within a conventional computer. The time meters preferably measure at a precision of $\frac{1}{100}^{th}$ to $\frac{1}{10,000}^{th}$ of a second. The elapsed time that each sensor is on during a single "blow" or exhalation, is in turn transferred to a device 34 which includes at least a storage device for recording when and how long each sensor was on during a single blow. Multiple blows can also be retained in storage. It is possible to incorporate into device 34 a computer for processing the data collected in storage. It is also possible to provide a port for downloading the data stored in device 34 to a remote computer either by a proximate link or by telephone, for example.

Figure 2:
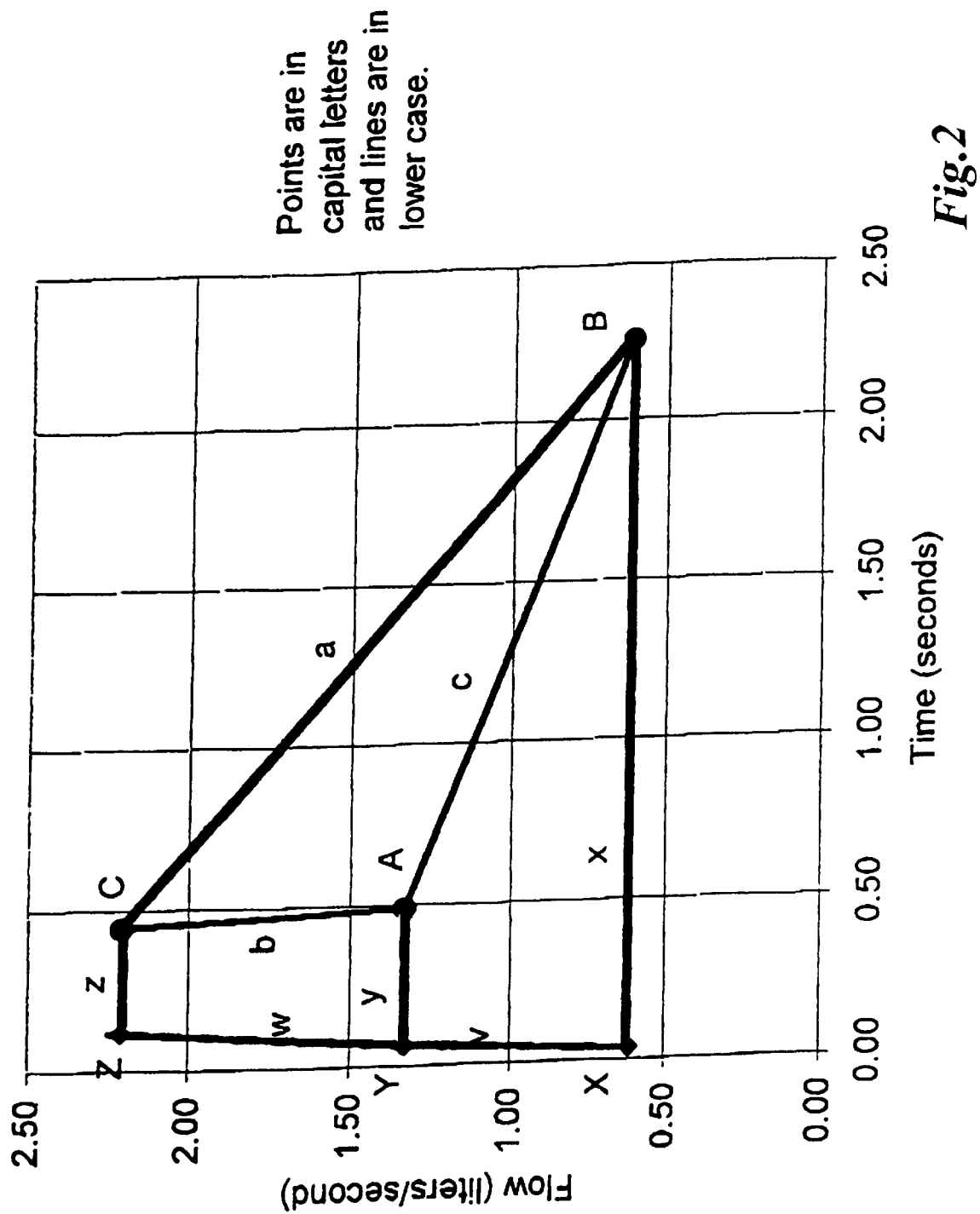
FIG. 2 is a graph showing an example plot of data obtained from the device of FIG. 1.

FIG. 2 is a graph of flow in liters per second versus time and seconds for a sample blow. Sensor 22 is set to switch on when the flow rate of the blow has risen to 0.62 liters per second and sensor 22 has been switched on (shown in FIG. 2 at X). At B, the flow rate has passed below 0.62 liters per second and sensor 22 has been switched off. With respect to sensor 24, FIG. 2 shows the analogous points to X and B at Y and A, respectively. With respect to sensor 26, the corresponding points are found at Z and C, respectively. It can be appreciated that additional sensors can be used at intermediate or alternate flow rates to better define the flow profile of the blow. The device has the capability of producing a sound when the switches turn on and off, identifying to the patient that the test is complete.

Various parameters can be calculated based upon data points A, B, C, X, Y, and Z. A number of these parameters or relationships are believed to be able to separate a population of patients with lung disease from a population of normal subjects with comparable age and size and sex, significantly more effectively than standard spirometric tests. The following relationships or parameters can be calculated based upon the data points previously described: The slope of the ascending flow rate line from the point of zero flow and zero time can be estimated; the sloop of lines a, b and c can be calculated, angles CBA and ACB and ABC can be calculated; the time duration of lines x, y and z can be determined; the lengths of lines u, w, a, b, and c can be calculated; the ratios x/c, w/b and (x+w)/a; and the time ratios z/y, z/x, y/x, and (x+y)/x can be calculated.

It is anticipated that various uses may be made of the data collected and the parameter relationships obtained based upon the data. These include: (1) spirometer studies of asthma and other respiratory diseased to detect exacerbations and to follow the course of the cronic illness and response to treatments; (2) home monitoring of asthma and other respiratory diseases; and (3) turning the patient and the ThAlRapy Bronchial Drainage Vest System®. In general, the pattern of activation and deactivation of the switches gives an indication of the best effort of the subject. The steeper the slope of the activation, the better the initiation of the expiratory effort The persistence of maximal effort is seen in the slope of deactivation with only rare slopes being greater than minus 4. The results of multiple blows are almost identical even the first time a subject uses the FlowTime spirometer.

The simplicity of the device makes it useful to test very small children and patients with limited strength. The resistance in the breathing tube 12 allows two precise decision criteria for an optimal test. First, specifically the slope of the line XYZ must approach the turbulent flow limitation of the breathing tube 12 and the line XYZ must be approximately straight. This defines the best start of the forced expiratory test. Second, the smaller the angle CAB, the better the effort in completing the entire forced expectory test.

EXAMPLE 1

FTM device 10 was tested on 66 control subjects, age 18 to 40, and 44 Cystic Fibrosis patients, age 14 to 50. They all have performed standard Spirometry test followed by Flow Time Monitoring (FTM). Results show a strong separation of Cystic Fibrosis from normal subjects for FTM. The majority of the Cystic Fibrosis data fall outside the 95% confidence limits of the normal range. This separation is not as pronounced when using standard spirometrics parameter.

Figure 3:
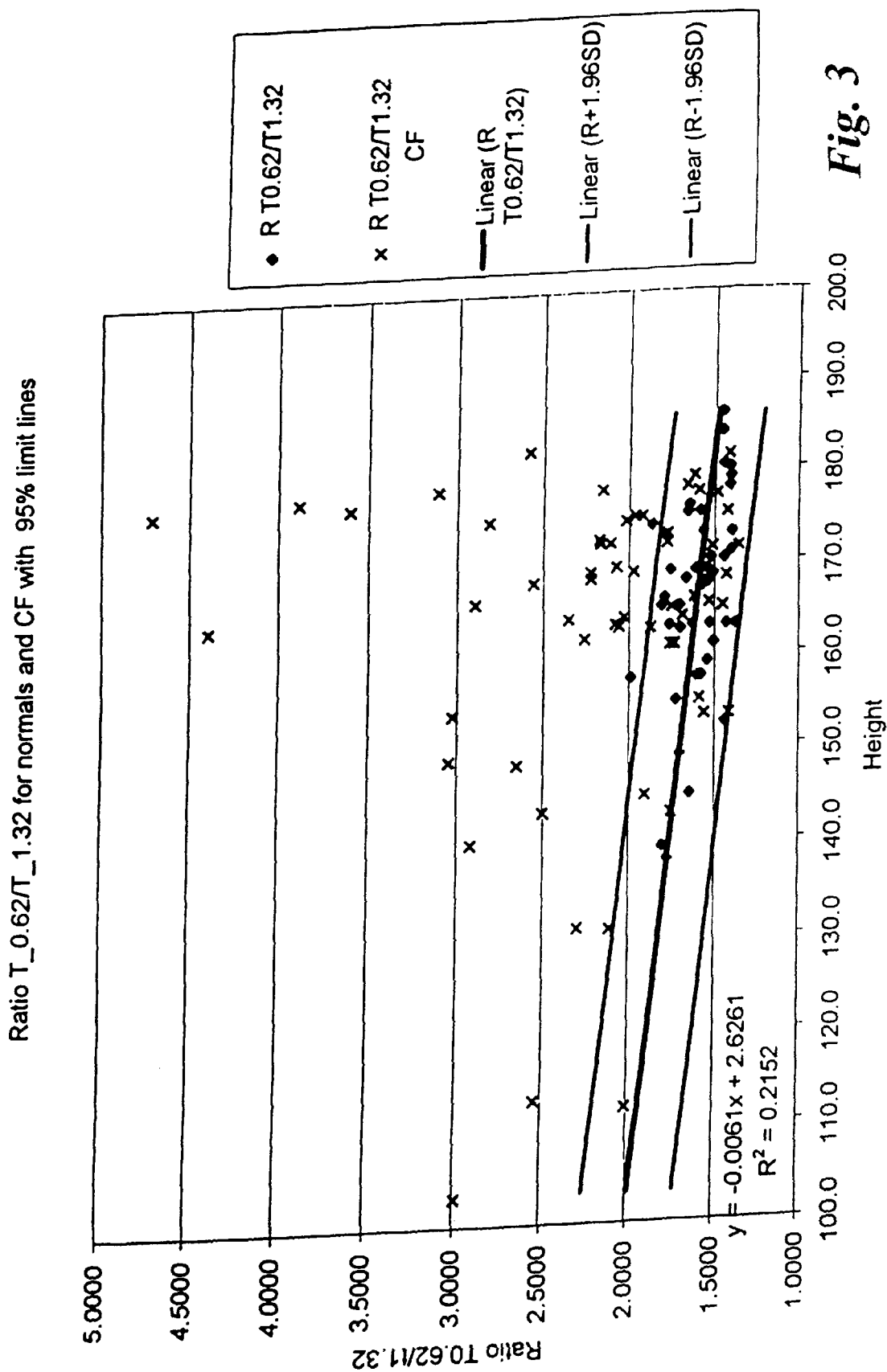
FIG. 3 is a graph of the ratio of $T\_0.62/T\_1.32$ for normal subjects and Cystic Fibrosis subjects as a function of height.
Figure 4:
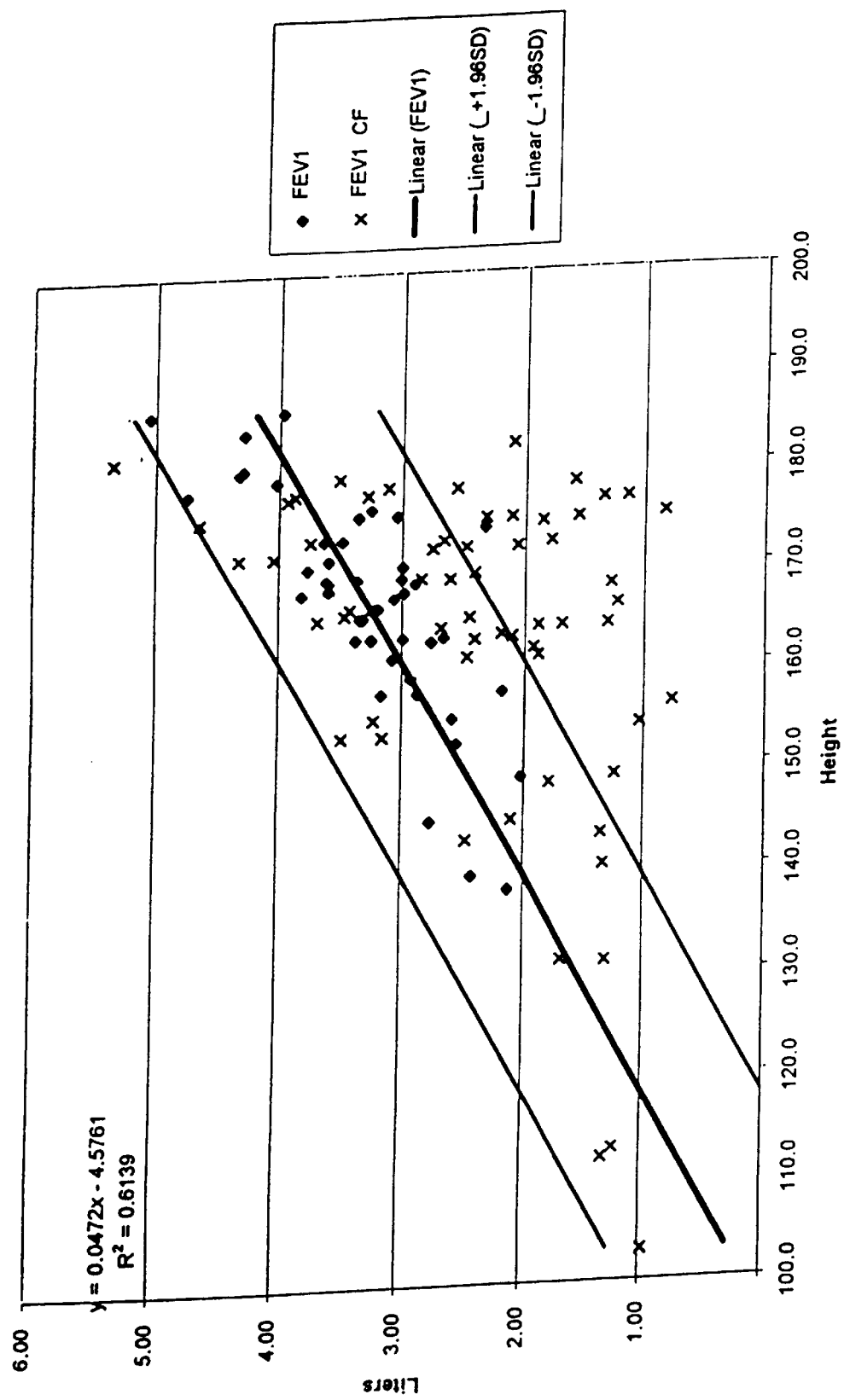
FIG. 4 is a graph of FEV1 for normal subjects and Cystic Fibrosis subjects as a function of height.

FIGS. 3 and 4 show separation of normal subjects from Cystic Fibrosis patients using FTM ratios T_0.62/T_1.32 (x/y on FIG. 2) and standard FEVI measurement respectively. FIG. 3 shows Cystic Fibrosis patients ("x") data lies outside of the 95 percent (95%) confidence lines more than the Cystic Fibrosis data in FIG. 4. The control subject results are indicated by the diamonds.

Trigger points of pressure switches was consistent and data acquisition was reliable. Results in FIGS. 3 and 4 show plots with the same Y-axis representing the study subjects height (cm) and X-axis representing different variables collected from FTM and standard Sprirometer test. It is believed that different variables other than height (ratio T_0.62/T_1.32) used on the X-axis, a separation of Cystic Fibrosis from the normal group can be seen more distinctly in the FTM than the standard Spirometer.

When the FTM device is used to "tune" a ThAIRapy vest at home, the following procedure can be followed:

1. Inspire to TLC.
2. Exhale at about 0.51/sec.
3. Actuate vest at start of exhalation at a trial frequency.
4. Check time when flows were >2.21, 1.33 and 0.63 L/sec.
5. Repeat at a different vest frequency.

The cycle can be repeated at a different frequency until the largest times for flows greater than 2.21, 1.33 and 0.63 L/sec are determined. The greater the time flows at each flow rate the better the vest is tuned. This process could be repeated manually or automated by logic control circuitry.

A patient using the FTM device 10 at home could bring the device 10 to the Emergency room to download date, time and flow time data stored in device 34 for days or weeks before an emergency. After the patient receives ER therapy, the FTM could be performed again to compare the results with the historic data download.

Numerous characteristics and advantages of the invention covered by this document have been set forth in the foregoing description. It will be understood, however, that this disclosure is, in many respects, only illustrative. Changes may be made in details, particularly in matters of shape, size and ordering of steps without exceeding the scope of the invention. The invention's scope is, of course, defined in the language in which the appended claims are expressed.

What is claimed is:

1. A device for measuring pulmonary function, comprising:

an elongate breathing tube having an inside diameter of less than about 15 mm;

a first sensor in fluid communication with the flow tube:

wherein the first sensor is activated at a first pressure level and remains activated so long as the pressure exceeds the first pressure level;

a second sensor in fluid communication with the flow tube;

wherein the second sensor is activated at a second pressure level and remains activated so long as the pressure exceeds the second pressure level; and timing means for determining the time that each sensor is activated when a person blows into the tube.

2. The device in accordance with claim 1, wherein the first sensor activates at between about 0.125 to 0.373 kPa.

3. The device in accordance with claim 1, wherein the first sensor and the second sensor each comprise a pressure transducer.

4. The device in accordance with claim 1, wherein the inside diameter of the tube is approximately 9.5 mm.

5. The device in accordance with claim 1, wherein the inside diameter of the tube is between about 2 and 15 mm.

6. A method of measuring pulmonary function, comprising the steps of:

providing a pulmonary function device including a blow tube fluidly connected to a plurality of pressure sensitive sensor wherein at least two of the sensors are activated at different pressure levels;

measuring the time that each pressure sensor is activated while a person blows into the blow tube; and comparing the time that the sensors are activated while the person is blowing into the blow tube with a reference set of time data for a group of subjects.

7. The method in accordance with claim 6, wherein the group of subjects is a control group.

* * * * *